(12) United States Patent
Shiang et al.

(10) Patent No.: US 6,509,373 B1
(45) Date of Patent: Jan. 21, 2003

(54) STRAIN OF STREPTOMYCES, AND RELEVANT USES THEREOF

(75) Inventors: Ming Shiang; Mann Yan Kuo; Kuei Chih Chu; Pao Chi Chang; Hsiu Ying Chang; Hai Ping Lee, all of Taipei (TW)

(73) Assignee: Development Center for Biotechnology (TW)

( * ) Notice: Subject to any disclaimer, the term of this patent is extended or adjusted under 35 U.S.C. 154(b) by 0 days.

(21) Appl. No.: 09/569,878

(22) Filed: May 12, 2000

Related U.S. Application Data

(62) Division of application No. 09/133,837, filed on Aug. 13, 1998, now Pat. No. 6,193,964.

(30) Foreign Application Priority Data

Jan. 16, 1998 (CN) .......................................... 87100574 A

(51) Int. Cl.⁷ ............................................. A61K 31/275
(52) U.S. Cl. ........................ 514/519; 514/529; 424/122
(58) Field of Search ................................ 424/93.43, 122; 435/253.5, 169; 514/519, 529

(56) References Cited

U.S. PATENT DOCUMENTS 3,674,774 A 7/1972 Williams et al. .............. 536/53

FOREIGN PATENT DOCUMENTS

| DE | 2 019 838 | | 4/1970 |
| DE | 3607287 | * | 1/1988 |

OTHER PUBLICATIONS

Copy of German Office Action dated Aug. 27, 2001, and copy of English–language translation.

* cited by examiner

Primary Examiner—Jean C. Witz
(74) Attorney, Agent, or Firm—Finnegan, Henderson, Farabow, Garrett & Dunner, L.L.P.

(57) ABSTRACT

Disclosed is a new *Streptomyces candidus* strain, and relevant uses thereof.

1 Claim, 5 Drawing Sheets

STRAIN OF STREPTOMYCES, AND RELEVANT USES THEREOF

This is a division of application Ser. No. 09/133,837, filed Aug. 13, 1998, now U.S. Pat. No. 6,193,964 which is incorporated herein by reference.

FIELD OF THE INVENTION

The invention relates to a novel strain of Streptomyces sp., designated *Streptomyces candidus* Y21007-2; a conditioned medium of the strain; the uses of the medium; a method for producing borrelidin utilizing the strain; and the novel uses of borrelidin.

BACKGROUND OF THE INVENTION

Fungal phytopathogen is one of the causes leading to severe economic losses in the agricultural and horticultural industries. Infected plants show inhibited germination and growth, and soft rot, or die. In addition, soils infested with phytopathogenic fingi may be unsuitable for growing certain crops.

Phytophthora spp. is an important soil-borne fungal phytopathogen, which causes diseases to a broad host range, e.g. stalk and leaf lesions of melons and fruits. The infected parts of plants exhibit water-infiltrated lesions at the initial stage. The lesions will rapidly turn brown, and rotten. If the moisture remains high, a large amount of white fungal mass will grow and result in rotten, hollow fruits with brown spots. The seedlings of plants will die immediately after being infected with Phytophthora spp. Once infected, the stems and leaves of plants above the ground will turn yellow and harden, or wilt.

Pythium spp. is another important soil-borne fungal phytopathogen, which causes diseases to the seedlings of Cruciferae spp. and melons. Seeds at the emerging stage infected with the pathogen will not emerge or become rotten. Infected seedlings will exhibit water-infiltrated lesions at the infected parts, wilt and die. For the damping-off seedlings, the infected tissues are brown, dried, thinned, and stunted.

Currently, fungicides widely used for treating Phytophthora and Pythium infections are chemical agents, including Etridiazole (also known as Terrazole), Previcur N (also known as Propamocarb hydrochloride), Metiram (also known as Rinclozolin), Ridomil (also known as Metalzaxyl), Mertect (also known as Thiabendazole), Oxine-Copper (also known as Quinolate), Dithane M-45 (also known as Mancozeb) and Dithane Z-78 (also known as Zineb).

Due to the intensive use, the strains resistant to some of the above chemical fungicides have been reported, e.g. *Phytophthora megasperma* f. sp. medicaginis tolerant to Ridormil (see R. M. Hunger et al., Plant Dis. 66:645–649 (1982)).

Moreover, the environmental protection has drawn the international attentions. In viewing that the abuse of chemical fungicides is ecologically detrimental, there is a need to develop environmentally acceptable biological agrochemicals.

Borrelidin is a macrolide antibiotic, which was first isolated by Berger et al. in 1949 from the culture medium of *Streptomyces rochi* and reported to be active against borrelia, the relapsing fever spirochete, and capable of enhancing the activity of penicillin G against syphilis spirochete. See J. Berger et al., Arch. Biochem. Biophys. 22:476–478 (1949).

Borrelidin-producing strains and new uses of the antibiotic have been subsequently identified in the art. For instance, M. Lumb et al., Nature 206:263–265 (1965) describes borrelidin produced by *S. griseus* C2989 strain as an antiviral agent which is inactive against bacteria; V. Prikrylova et al., Physiological Aspects 34:422–423 (1989) reports a new strain of *S. rochi* which produces borrelidin as a substance inhibiting germination of plant seeds; and DE 36 07 287 A1 discloses borrelidin produced by a new *S. griseus* strain as a pesticide and herbicide.

U.S. Pat. No. 4,759,928 discloses an antibacterial material produced by *S. albovinaceus* which is active against *Treponema hyodysenteriae*. The antibacterial material is latter identified as borrelidin. See H. Maehr et al., The Journal of Antibiotics, Vol. XL No. 10, pp. 1455–1456 (1987).

Borrelidin has been chemically characterized and identified as 2-[7-cyano-8,16-dihydro-9,11,13,15-tetramethyl-18-oxooxacyclooctadeca-4,6(E, Z)-diene-2-yl] cyclopentacarboxylic acid with the following structure:

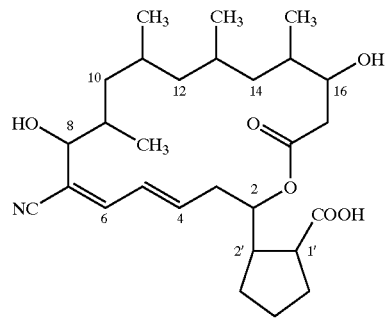

See M. Kuo et al., The Journal of Antibiotics, Vol XLII NO. 6, pp. 1066–1077 (1989).

The above references and patents, however, do not disclose the antifungal activity of borrelidin, and are herewith incorporated as the references of the application.

SUMMARY OF THE INVENTION

A new *Streptomyces candidus* strain, designated *Streptomyces candidus* Y21007-2, has been surprisingly found. The conditioned medium of the strain is found to be active against fungi and capable of promoting the germination of seeds.

Therefore, in the first aspect of the invention, the novel strain *Streptomyces candidus* Y21007-2 is provided.

In the second aspect of the invention, the conditioned medium of the novel strain is provided.

In a further aspect of the invention, the uses of the above conditioned medium as a fungicide and as a seed germination stimulator are provided.

The active ingredient in the conditioned medium of *Streptomyces candidus* Y21007-2 has been identified as borrelidin.

Accordingly; in a still further aspect of the invention, there is provided a method for producing borrelidin which comprises cultivating the novel strain *Streptomyces candidus* Y2 1007-2.

The invention also provides the novel uses of borrelidin as a fungicide and as a seed germination stimulator.

IDENTIFICATION AND CHARACTERIZATION OF THE MICROORGANISM

The novel Y21007-2 strain was isolated from a soil sample taken from Peng-Hu, Taiwan, ROC. The microorganism has been identified by the Food Industry Research and Development Institute, Shin-Chu, Taiwan, ROC as a strain of *Streptomyces candidus*. The methods and results are as follows:

Taxonomic and morphologic characterization was made using the methods recommended by the International Streptomyces Project (ISP) for characterizing Streptomyces species.

1. Cell Wall Analysis

Cells taken from the culture medium (1–2 mg) were put into a test tube containing one drop of 6N HCl, and heated to 121° C. for 15 min. Thin layer chromatography (TLC) was conducted with methanol-H$_2$O-conc. HCl-pyridine. Ninhydrin was then applied. Diaminopimelic acid (DAP) will result in a yellowish green color, while other amino acids produce a purple red color. See T. Hasegawa et al., "A Rapid Analysis for Chemical Grouping of Aerobic Actinomycetes," J. Gen. Appl. Microbiol. 29:319–322 (1983).

2. Whole Cell Sugar Analysis

Cells taken from the culture medium (1–2 mg) were put into a test tube containing 0.25N HCl, and heated to 121° C. for 15 min. TLC was conducted with n-butanol-H$_2$O-pyridine-toluene. Aniline phthalate was applied to develop the color of sugars. See T. Hasegawa et al., (1983), supra.

3. Cultural Characteristics Analysis

Cells were cultured on yeast extract-malt extract agar (ISP #2 medium), oatmeal agar (ISP #3 medium), inorganic salts starch agar (ISP #4 medium), and glycerol-asparagine agar (ISP #5 medium), respectively for 14 days to observe the vegetative mass, aerial mass, spore production and pigment production. See E. B. Shirling et al., "Methods for Characterization of Streptomyces Species," Int. J. Syst. Bacteriol., 16:313–340 (1966).

4. Melanoid Pigment Production Analysis

Cells were cultured on tryptone-yeast extract broth (ISP #1 medium), peptone-yeast extract iron agar (ISP #6 medium) and tyrosine agar (ISP #7 medium) for 14 days, respectively to observe the melanoid pigment production. See E. B. Shirling et al., (1966), supra.

5. Morphological Characteristics Analysis

Cells together with agar were cut from ISP #3 and #4 media, dehydrated in oven for I day, and coated with gold in an ion-coater. Morphology was studied using a scanning electron microscope (SEM). See E. B. Shirling et al., (1966), supra.

6. Sugar Utilization Analysis

Cells were cultured on ISP #9 medium containing 1% D-glucose, L-arabinose, D-xylose, sucrose, D-fructose, raffinose, rhamnose, I-inositol, D-mannitol, cellulose and salicin, respectively for 14 days to observe cell growth. Culture media with D-glucose or without any sugar were used as controls. See E. B. Shirlin et al., (1966), supra.

Figure 1:
FIG. 1 is a scanning electron micrograph of *S. candidus* Y21007-2 sporophore.
Figure 2:
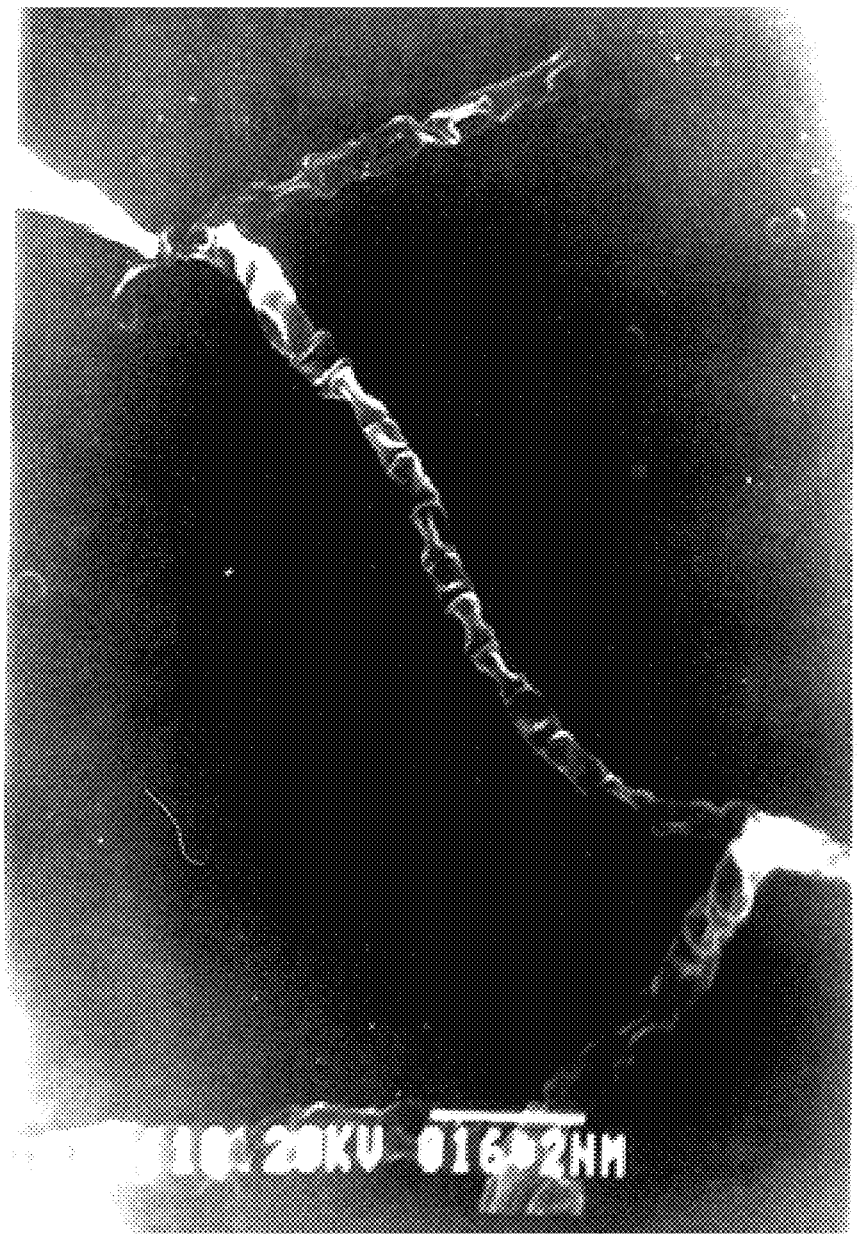
FIG. 2 is a scanning electron micrograph of *S. candidus* Y21007-2 spore chain.
Figure 3:
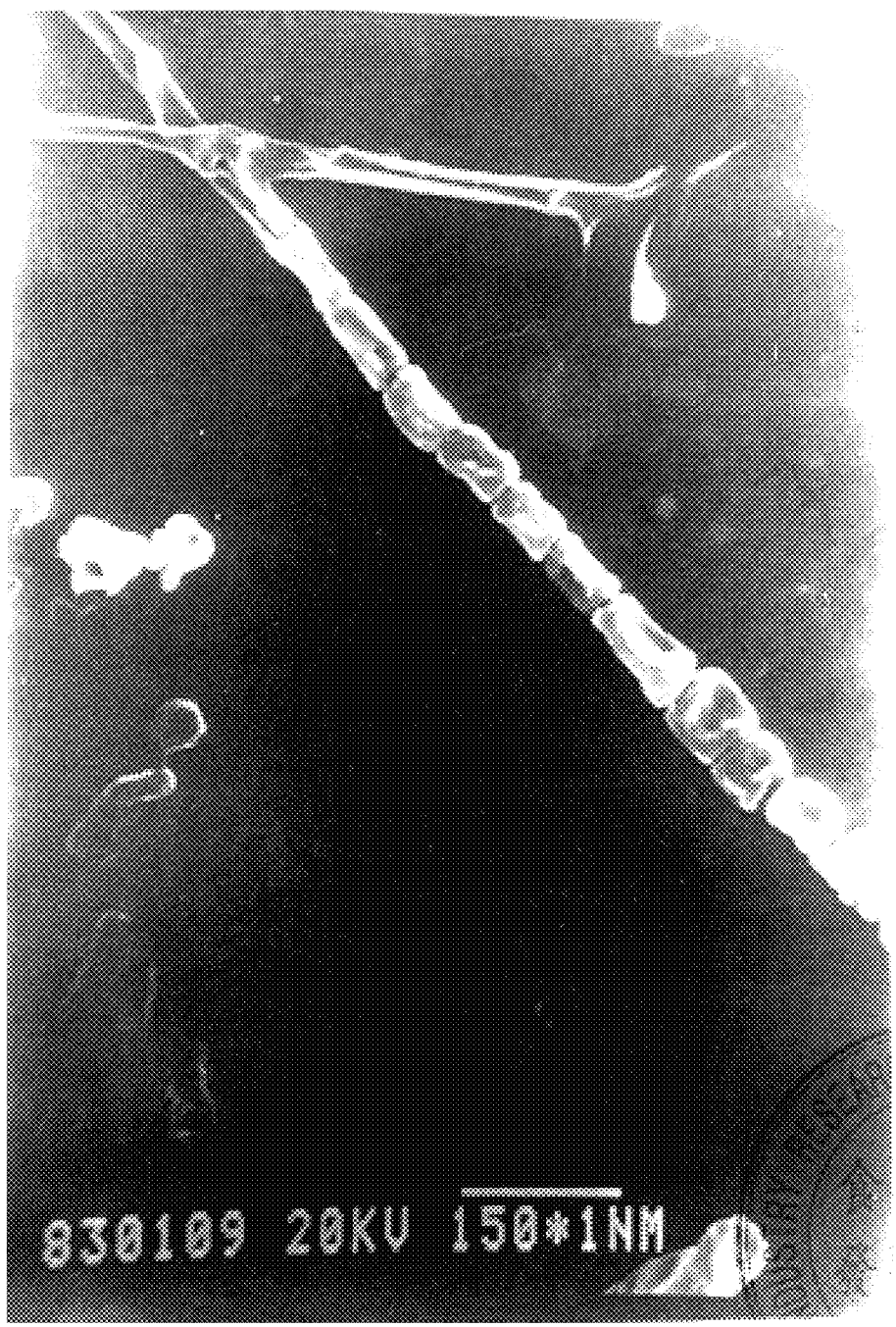
FIG. 3 is a scanning electron micrograph of *S. candidus* Y21007-2 spore surface.

The results are shown in Table 1 and FIGS. 1–3.

TABLE 1

Morphological and Physiological Characteristics of Y21007-2

| Characteristics Tested | Results |
| --- | --- |
| Aerial mass color | Grayish white |
| Vegetative mass color | Yellow to yellowish brown |
| Soluble pigment | Not produced |
| Melanoid pigment production | None |
| Spore chain | Linear, 7–50 spores per sporophore |
| Spore surface | Smooth, without adherent materials |
| D-glucose | + |
| L-arabinose | + |
| D-xylose | + |
| Sucrose | − |
| D-fructose | + |
| Raffinose | − |
| Rhamnose | + |
| I-inositol | − |
| D-mannitol | + |
| Cellulose | − |
| Salicin | + |
| Identification | *Streptomyces candidius* |

Cell Wall Amino Acid and Whole Cell Sugar Analyses

The cell wall amino acid and whole cell sugar contents of Y21007-2 are LL-DAP and a small amount of xylose, respectively. The strain belongs to chemotype IC according to the classification by M. P. Lechevalier et al., "The Chemotaxonomy of Actinomycetes." In: Dietz, A., and D. W. Thayer. (eds) Actinomycete Taxonomy. SIM Special Publication No. 6 USA, and is assigned to the genus Streptomyces.

Cultural Characteristics

Y21007-2 grows well in ISP #2–5 media. The spore production on ISP #5 medium is poor, but that on other media is good. The aerial mass color is grayish white, and the vegetative mass color is yellow to yellowish brown. No soluble pigment or melanoid pigment is produced.

Morphological Characteristics

The spore chain of Y21007-2 is linear (FIG. 1), with 7–50 spores per sporophore (FIG. 2). The surface of spore is smooth without adherent materials.

Physiological Characteristics

Y21007-2 utilizes D-glucose, D-fructose, D-xylose, L-arabinose, rhamnose, D-mannitol and salicin, and does not utilize sucrose, raffinose, cellulose and I-inositol.

Species Identification

The classification described by H. Nonomura, "Key for Classification and Identification of 458 Species of the Streptomycetes Included in ISP." J. Ferment. Technol. 52:78–92 (1974) is used for identification of Y21007-2. The microorganism is similar to both *S. candidus* and *S. albovinaceus*. The comparison with standard isolate of the strains (E. B. Shirling et al., "Cooperative Description of Type Cultures of Streptomyces. II. Species Descriptions from First Study." Int. J. Syst. Bacteriol. 18:69–189 (1968); and E. B. Shirling et al., "Cooperative Description of Type Cultures of Streptomyces. III. Additional Species Descriptions from First and Second Studies." Int. J. Syst. Bacteriol. 18:279–393 (1968)) reveals that Y21007-2 is most related to *S. candidus*. The strain is identified as a new strain in the species.

Deposition Information

One culture of *Streptomyces candidus* Y21007-2 has been deposited with the American Type Culture Collection, (ATCC, 10801 University Boulevard, Manassas, Va. 20110-2209, USA) on Jul. 2, 1998 in accordance with the Budapest Treaty, and assigned the accession No. ATCC 202148.

DETAILED DESCRIPTION OF THE INVENTION

The invention in the first aspect provides a biologically pure culture of *Streptomyces candidus* Y21007-2.

It is known in the art to obtain mutants of microorganisms without altering the characteristics thereof. For instance, mutants may be obtained by treatment with physical or chemical mutagens, such as UV light, X-rays, gamma-rays and chemicals such as n-methyl-N'-nitro-N-nitrosoguanidine. It is also known in the art to obtain natural variants by e.g. screening cultures of the parent strain. Therefore, the invention also pertains to the mutants or variants of *S. candidus* Y21007-2 which retain the characteristics of the strain.

Y2 1007-2 of the invention may be cultured with any methods known in the art for culturing Streptomyces species, e.g. aerobic cultivation on agars or submerged aerobic fermentation in fermentors. Preferably, the strain is submerged fermented.

The media for growth or fermentation may contain assimilable carbon sources and digestible nitrogen sources. Suitable carbon sources include, but not limited to, glucose, lactose, mannitol, dextrin, corn, starch, xylose, fructose, lactose and the like.

Suitable nitrogen sources include, but not limited to, natural nitrogen-containing materials and the products thereof, e.g. meat extracts, peptones, corn infiltration solutions, yeast extracts, soy bean meals, tryptones, cotton seed meals, wheat meals, and the like. Organic or inorganic nitrogen-containing materials may also be used, e.g. urea, nitrates and ammonium salts, such as sodium nitrate, ammonium acetate, ammonium chloride, ammonium sulfate, ammonium phosphate, and the like.

Optionally, the media for cultivating Y21007-2 may also contain inorganic salts, trace elements, and growth stimulators.

The inorganic salts suitable for use in the media for cultivating Y21007-2 include, but not limited to, the salts capable of yielding zinc, sodium, magnesium, calcium, ammonium, chloride, carbonate, sulfate nitrate, and the like.

In addition, essential trace elements necessary for the growth and development of the organism may also be included in the culture media. Such trace elements commonly occur as impurities in other components of the media in an amount sufficient to meet the growth requirements of the organism.

The growth stimulators suitable for use in the invention include, but not limited to, glycerol and sodium salts, such as sodium acetate, sodium glutamate, sodium tartarate, and the like.

The term "conditioned medium" used in the specification refers to the whole contents in a flask or fermentor, including both the cellular and non-cellular components, resulted directly from the fermentation of Y21007-2 in an appropriate culture medium without being subject to filtration, separation or purification.

In general, a substantial quantity of Y21007-2 conditioned medium may be obtained by fermentation in both flask and fermentor. Preferably, the fermentation is conducted in a fermentor.

In accordance with the invention, the fermentation for obtaining a substantial quantity of conditioned medium is conducted under aerobic conditions at a temperature between about 15° C. to about 45° C., preferably between about 25° C. to about 35° C., and the most preferably at about 30° C.

As is customary in aerobic culture processes, sterile air is blown into the vessel from the bottom while the medium is stirred with conventional turbine impellers. In general, the aeration rate and agitation rate should be sufficient to maintain a level of dissolved oxygen of at least 30% of air saturation with an internal vessel pressure of 0.2 bar.

The pH value in the fermentor varies along with the culture media and the quantity of inocula used. Typically, the pH value is maintained from weakly acidic to basic. If necessary, prior to inoculation or during the fermentation, the pH value in the fermentor can be appropriately adjusted to be weakly acidic to basic, e.g. about pH 6.0 to about pH 9.0. Preferably, the pH value prior to inoculation is adjusted to about pH 6.5 to about pH 8.5, most preferably about pH 7.5 to about pH 8.5.

Any basic materials known in the art can be used to adjust the pH value, e.g. alkaline metal salts, such as sodium salts, and the like.

In principle, the time for cultivating *Streptomyces candidus* Y21007-2 should be sufficient to produce a sufficient amount of conditioned medium with desired activity. In general, the cultivation is conducted for about 24 to about 144 hours, preferably, about 60 to about 120 hours, and most preferably about 72 to about 96 hours.

Furthermore, anti-foam agents can be appropriately added during the fermentation to inhibit excessive foam formation. For instance, polypropylene glycol of a molecular weight of about 2000 can be added to the culture medium at an amount of about 0.2 g/liter of culture medium.

Borrelidin has been isolated from the conditioned medium of *Streptomyces candidus* Y21007-2 of the invention. Accordingly, the invention in a further aspect relates to a process for producing borrelidin which comprises cultivating *Streptomyces candidus* Y21007-2 of the invention, or the mutants or variants thereof.

Because of the time lag commonly associated with the inoculation of large fermentors with spore form organisms, it is preferable to use a vegetative inoculum prepared by inoculating a small volume of culture medium with the spore form or mycelial fragments thereof to obtain fresh, actively growing cultures of the organism. The vegetative inoculum is then transferred to a larger vessel, and the production stage of the desired antibiotic is then initiated.

The media suitable for cultivating Y21007-2 stock culture include, but not limited to, potato dextrose broth (PDB), nutrient broth (NB), NGY culture medium (containing 8 g/liter of NB, 10 g/liter of glucose and 5 g/liter of yeast extract), and SL culture medium (containing 10 g/liter soy bean protein and 5 g/liter lactose).

The media suitable for fermenting Y21007-2 in a fermentor include, but not limited to, NGY and SS culture medium (containing 30 gliter of soy bean protein and 30 g/liter of starch).

After fermenting Y2 1007-2 in accordance with the invention, the conditioned medium thereof can be directly used, or formulated as biological fungicides.

Alternatively, borrelidin can be recovered from the conditioned medium in a manner known in the art. For instance, the active ingredient can be extracted with solvents, and purified with chromatography. The solvents suitable for separating the active ingredient in accordance with the invention include, but not limited to, methanol, acetic acid, acetone, water and acetic acetate, or the mixture thereof. Preferably, acetic acetate is used. Suitable chromatography includes thin layer chromatography and silica column chromatography.

In accordance with the purposes for application, the conditioned medium or purified borrelidin in accordance with the invention can be used directly or formulated as compositions suitable for spraying, atomizing, dusting, spreading or pouring. For instance, the compositions can be formulated as ready-to-spray solutions, powders, suspensions, highly concentrated aqueous, oily or other suspensions or dispersions, emulsions, oil dispersions, pastes, dusts, or granules.

The compositions may be prepared in a known manner, e.g. by extending the active ingredient with agriculturally acceptable carriers, auxiliaries or diluents, such as solvents, emulsifiers and dispersants or surfactants.

Solvents suitable for use in the invention include, but not limited to, aromatics, e.g. xylene; chlorinated aromatics, e.g. chlorobenzenes; paraffins, e.g. mineral oil fractions; alcohols, e.g. methanol and butanol; ketones, e.g. cyclohexanone; amines; e.g. ethanolamine and dimethylformamide; and water. When water is used, other organic solvents may also be used as co-solvents.

Carriers suitable for use in the invention include, but not limited to, ground natural or synthetic minerals, e.g. kaolins, clays, talc, chalk, silica, silicates, and the like.

Emulsifiers suitable for use in the invention include, but not limited to, nonionic and anionic emulsifiers, e.g. polyoxyethylene fatty alcohol ethers, alkylsulfonates, arylsulfonates, and the like.

Dispersants suitable for use in the invention include, but not limited to, lignosulfite waste liquors and methylcellulose; and the like.

Suitable surfactants include, but not limited to, lignophenol-, naphthalene- and dibutylnaphthalenesulfonic acid, and of fatty acids, alkyl- and alkylarylsulfonates, alkyl lauryl ether and fatty alcohol sulfates, and salts of sulfated hexa-, hepta- and octadecanols and of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated iso-octyl-, octyl- or nonylphenol, alkylphenol polyglycol ethers, tributylphenyl polyglycol ether, alkyllauryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

The fungicidal composition of the invention is specific to Phytophthora and Pythium, and therefore can be used to treat and prevent the diseases caused by the two genera, e.g. Phytophthora blight of pepper (*P. capsici* Leonian), Pythium fruit rot of cabbage (*P. aphanidermatum* Fitzpatrick), Phytophthora blight of flaceray gervera (*Gerbera jamesonii*) and orchid caused by e.g. *phytophthora capsicis, Phytophthora cinnamomi, Pythium aphanidermatum, Pythium splendens, Pythium spinosum* and *Pythium sylvaticum*.

The crops suitable for use in accordance with the invention for fungal diseases treatment and prevention and for seed germination stimulation include, but not limited to, tomato, egg plant, green pepper, cucumber, water melon, pumpkin, cabbage, garden pea, flaceray gervera, orchid and the like.

In general, the seeds, plants or soils infected with, or susceptible to, fungal infections are treated with a fungicidally or germination-stimulatorily effective amount of the active ingredient. For instance, the conditioned medium or composition of the invention can be sprayed, spread or poured onto the plants, seeds or soils to be treated, or mixed with the soils to be treated.

The composition of the invention generally comprises about 0.01 to about 1 wt % of the active ingredient, preferably about 0.05 to about 0.1 wt %. For fungal treatment and prevention, the composition is applied at the rate of about 1 to about 20 Kg/acre, preferably about 5 to about 10 Kg/acre. For seed germination stimulation, the composition is applied at the rate of about 5 to about 10 Kg/acre.

To enhance the application efficiency, the fungicidal composition of the invention may also comprise other active ingredients, such as herbicides, insecticides, growth stimulators, fertilizers, and the like.

To extend the fungicidal effect, the fungicidal composition of the invention may also comprise other fungicides to result in a widening of the fungicidal spectrum of action. Alternatively, the fungicidal composition of the invention can be alternated with fungicides comprise other fungicidal ingredients that widen the fungicidal spectrum of action.

The active ingredients suitable for combined use or alternate use with the fungicidal composition of the invention include, but not limited to, anilinpyrimidine, azole, morpholine, strobilurins, cyanopyrrolphenyl carbamate, pyridine, and the like.

EXAMPLE 1

Flask Fermentation of Y21007-2

Y21007-2 stock culture was cultivated on PDA at 30° C. for 3 weeks before fermentation.

A loop of microorganism was taken from PDA, and inoculated to a 500 ml flask containing 100 ml NGY or SL. The microorganism was cultivated at 30° C., 200 rpm for 48 hours. The culture was transferred to another 500 ml flask containing 100 ml SS medium with an inoculation rate of 8%, and cultured for 72 hours. The amount of borrelidin analyzed with HPLC (A) is shown in Table 2.

TABLE 2

| Medium | (A), mg/l |
| --- | --- |
| SL | 15.61 |
| NGY | 23.95 |

EXAMPLE 2

Tank Fermentation of Y21007-2

The microorganism was cultured in a manner similar to Example 1, except that the culture was transferred to a 20-liter Chemap fermentor containing SS medium and cul tured for 72 hours. The amount of borrelidin analyzed with HPLC (A) is shown in Table 3.

TABLE 3

| Medium | (A), mg/l |
|---|---|
| SL | 24.19 |
| NGY | 22.45 |

EXAMPLE 3

Fermentation with Stimulators

In SS media added with 0.1% sodium acetate, sodium glutamate or sodium tartarate, Y21007-2 was cultured at 30° C., 200 rpm for 72 hours. A similar medium without additives was used as control. The amount of borrelidin was analyzed with HPLC. The results are shown in Table 4.

TABLE 4

| Stimulator | (A), mg/l |
|---|---|
| Sodium Acetate | 15.12 |
| Sodium Glutamate | 15.78 |
| Sodium Tartarate | 16.76 |
| Control | 12.23 |

EXAMPLE 4

Germination Stimulation Activity Test

The plants tested include garden pea (15 seeds/pot) and cabbage (200 seeds/pot). The soil screened though #4 mesh was thoroughly mixed with fertilizer at the ratio of 40:1. Each pot was placed with 200 g soil. The air-dried seeds disinfected with 1% NaOCl were evenly placed in each pot. Each pot was treated with the stock solution, 1.5× and 3× dilutions of the Y21007-2 conditioned medium obtained in Example 1, and covered with 50 g, soil. A pot without any treatment was used as control. The treatments were triplicated. After 7-day cultivation in green house, the rate of germination was recorded. The results are shown in Table 5.

TABLE 5

| Garden Pea | | Cabbage | |
|---|---|---|---|
| Concentration | Germination (%) | Concentration | Germination (%) |
| 10 ml | 67 | 10 ml | 54 |
| 20 ml | —* | 20 ml | 42 |
| 30 ml | 67 | 30 ml | — |
| Control | 40 | Control | 35 |

*Not Tested

As demonstrated in Table 5, Y21007-2 can promote the seed germination of garden pea and cabbage.

EXAMPLE 5

Broad Spectral Activity Test of Y21007-2 Conditioned Medium

Y21007-2 stock culture was cultivated on PDA at 30° C. for three days before use.

The colony was homogenized with a homogenizer and inoculated in a flask containing NGY medium. The cultivation was conducted at 30° C., 200 rpm for 72 hours, and transferred to a 20-liter fermentor containing SSM with an inoculation rate of 10% for additional 88-hour cultivation.

The conditioned medium was centrifuged at 13000 rpm, 40° C. for 15 min., and filtered through a 0.2 μm membrane. PDA media containing 25%, 10%, 5% and 1% filtrate were prepared, and placed into 24-well microtitration plates with an amount of 0.7 ml. The fungal mass to be tested was inoculated onto dried media at a diameter of 2 mm. The treatments were triplicated. The fungi were cultivated at an appropriate temperature. After the control group was covered with fungal mass, the diameters covered with fungal mass were recorded and converted to activity inhibition rate (%). The results are shown in Table 6.

TABLE 6

| | | Activity Inhibition (%) | | | |
|---|---|---|---|---|---|
| Fungi | Designation | 1 | 5 | 10 | 25 |
| Alternaria tenuis | AT | 42 | 61 | 67 | 80 |
| Botrytis cinerea | BC | 63 | 63 | 85 | 99 |
| Colletotrichum musae | CM | 17 | 28 | 39 | 53 |
| Fusarium oxysporum f.sp. (niveum) | FNC | 33 | 42 | 47 | 58 |
| Fusarium oxysporum f.sp. (niveum) | FO-WS2 | 25 | 33 | 39 | 61 |
| Fusarium oxysporum f.sp. (niveum) | FOR | 17 | 33 | 47 | 58 |
| Mycosphaerella sp. | CA-095-D | 22 | 53 | 61 | 95 |
| Phoma asparagi | PA100 | 67 | 70 | 75 | 92 |
| Phytophthora capsici | PC-AC10-2 | 83 | 92 | 92 | 99 |
| Phytophthora cinnamomi | PCI 29A' | 100 | 100 | 100 | 100 |
| Pythium aphanidermatum | PA | 78 | 83 | 100 | 100 |
| Pythium splendens | PSP-F9 | 94 | 100 | 100 | 100 |
| Pythium spinosum | PS | 0 | 0 | 22 | 50 |
| Pythium sylvaticum | PSY | 99 | 94 | 99 | 100 |
| Rhizoctonia solani AG1 | AG1 | 0 | 0 | 30 | 61 |
| Rhizoctonia solani AG2 | AG2 | 0 | 0 | 25 | 55 |
| Rhizoctonia solani AG4 | AG4 | 0 | 0 | 0 | 8 |
| Sclerotinia sclerotiorum | SS | 25 | 69 | 92 | 100 |
| Sclerotium rolfsii | SR | 25 | 42 | 67 | 92 |
| Sclerotium rolfsii B27 | SR-B27 | 30 | 53 | 72 | 97 |

As illustrated in the above table, the conditioned medium of Y21007-2 is specific to Phytophthora and Pythium.

EXAMPLE 6

Activity Inhibition Test of Y21007-2 on Phytophthora and Pythium

The conditioned medium of Y21007-2 was formulated to 10×, 20×, 40×, 80×, 160× and 320× dilutions in a manner similar to Example 5, and the activity inhibitions on P. aphanidermatum, P. splendens, P. sylvaticum, P. capsici and P. cinnamomi were tested. The results are shown in Tables 7–11.

TABLE 7

| P. aphanidermatum | |
|---|---|
| Concentration | Inhibition (%) |
| 10X | 100 |
| 20X | 100 |
| 40X | 100 |
| 80X | 100 |
| 160X | 100 |
| 320X | 100 |

TABLE 8

P. splendens

| Concentration | Inhibition (%) |
|---|---|
| 10X | 100 |
| 20X | 100 |
| 40X | 100 |
| 80X | 97 |
| 160X | 92 |
| 320X | 83 |

TABLE 9

P. sylvaticum

| Concentration | Inhibition (%) |
|---|---|
| 10X | 100 |
| 20X | 100 |
| 40X | 100 |
| 80X | 100 |
| 160X | 97 |
| 320X | 91 |

TABLE 10

P. capsici

| Concentration | Inhibition (%) |
|---|---|
| 10X | 99 |
| 20X | 97 |
| 40X | 99 |
| 80X | 99 |
| 160X | 92 |
| 320X | 92 |

TABLE 11

P. cinnamomi

| Concentration | Inhibition (%) |
|---|---|
| 10X | 100 |
| 20X | 100 |
| 40X | 100 |
| 80X | 100 |
| 160X | 100 |
| 320X | 100 |

EXAMPLE 7

Activity Against Phytophthora Blight of Pepper

Pepper seedlings were planted in pots (10 seedlings/pot) containing 150 g meshed soil. Each pot was poured with 10 ml P. capsici solution, and covered with 50 g additional soil. The conditioned medium obtained in Example 5 was diluted to 5×, and 30 ml was poured onto the test groups. The treatments were triplicated. Pots without receiving the mold solution were used as positive control, and those without receiving treatments were used as negative control. Surviving rates were recorded at weeks 1 and 2. The results are shown in Table 12.

TABLE 12

| | Surviving (%) | |
|---|---|---|
| Treatment | week 1 | week 2 |
| Y21007-2 5X | $97^{a1}$ | $90^{ab}$ |
| Etridiazole 2000X (175 ppm) | $87^{ab}$ | $83^{ab}$ |
| Positive Control | $63^b$ | $53^c$ |
| Untreated | $100^a$ | $97^a$ |

[1]Values followed by the same letter at each row are not significantly different at P = 0.05 according to Ducan's multiple range test As shown in the above table, the 5× dilution of Y21007-2 conditioned medium significantly increases at least 30% of the surviving rate of the tested plants infected with P. capsici.

EXAMPLE 8

Y21007-2 stock culture was cultivated on PDA at 30° C. for 3 days before use.

The colony was homogenized with a sterile homogenizer, and inoculated in a flask containing NGY. The microorganism was cultured at 200 rpm, 30° C. for 72 hours, and transferred to a 20-liter fermentor containing SS medium with an inoculation rate of 10% for an additional 72-hour cultivation.

Each pot containing 150 g meshed soil was poured with 10 ml P. aphanidermatum solution. Both the conditioned medium and filtrate of Y21007-2 were diluted to 5× and 20×. Each pot was poured with 30 ml of the dilutions. Some pots were stirred to evenly distribute the dilutions, while the others were not stirred. Cabbage seeds were placed in the pots (200 seeds/pot), and each pot was covered with 50 g additional soil. The treatments were triplicated. Etridiazole (2000×, about 175 ppm) was used as medicated control, and plants receiving no treatment as positive control. The surviving rate was recorded at week 2. The results are shown in Table 13.

TABLE 13

| | | (%) | |
|---|---|---|---|
| Treatments | | without mixing | with mixing |
| Y21007-2 | Conditioned medium | | |
| | 5X | $87^{a1}$ | $68^a$ |
| | 20X | $81^a$ | $62^a$ |
| Y21007-2 | Filtrate | | |
| | 5X | $81^a$ | $64^{ab}$ |
| | 20X | $80^a$ | $65^a$ |
| Etridiazole | 2000X (175 ppm) | $79^a$ | $60^a$ |
| Untreated | | $62^b$ | $45^b$ |

[1]Values followed by the same letter at each row are not significantly different at P = 0.05 according to Ducan's multiple range test

EXAMPLE 9

Isolation and Identification of Borrelidin

Procedure:
1. To the filtrate of conditioned medium (10 l), acetic acetate (10 l) was added. The mixture was stirred with magnetic overnight. The organic materials were extracted into the acetic acetate phase.
2. At 4° C., the mixture was centrifuged at 8 Krpm for 15 min. to separate the acetic acetate phase from the aqueous phase.
3. The acetic acetate phase was combined and concentrated to obtain the desired substance.
4. The substance obtained in Step 3 was dissolved in a small amount of $CHCl_3$. The solution was filtered to remove the insoluble and highly polar materials.

5. The filtrate was concentrated to dryness, and dissolved in methanol. The solution was filtered to remove the materials of a lower polarity.
6. The filtrate was concentrated to dryness. The crude product was dissolved in a small amount of methanol.
7. The crude product from Step 6 was chromatographed on Sephadex LH-20 (methanol) for several times. The small amount of purified materials was further purified by HPLC on $C_{18}$ column (methanol: 1% acetic acid=3:1; 0.9 ml/min.; UV 257 nm; retention time: 6.300). Repeated injections gave about 8 mg compound.

Results

Figure 4:
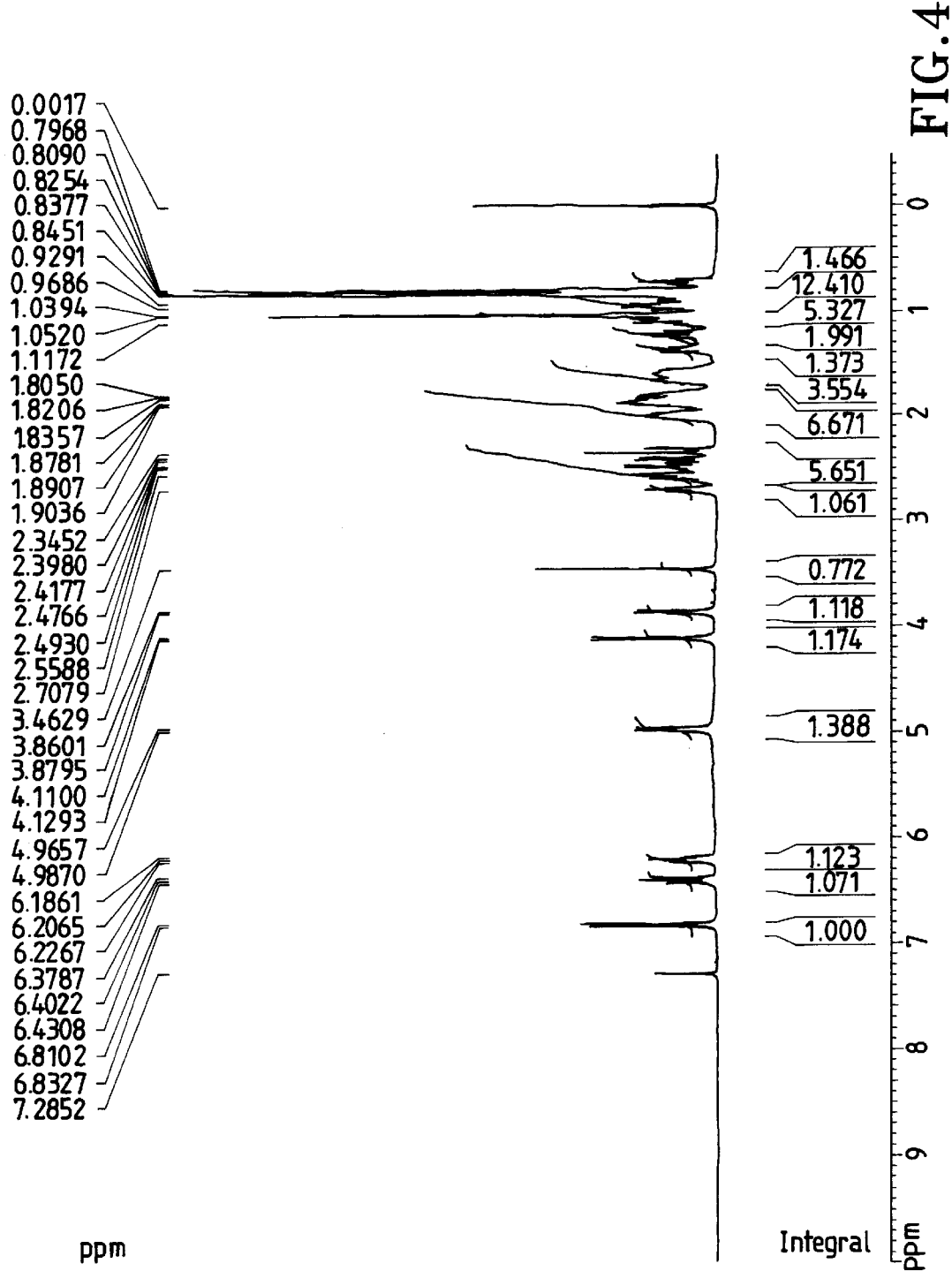
FIG. 4 is the $^1$H NMR spectrum of isolated borrelidin.
Figure 5:
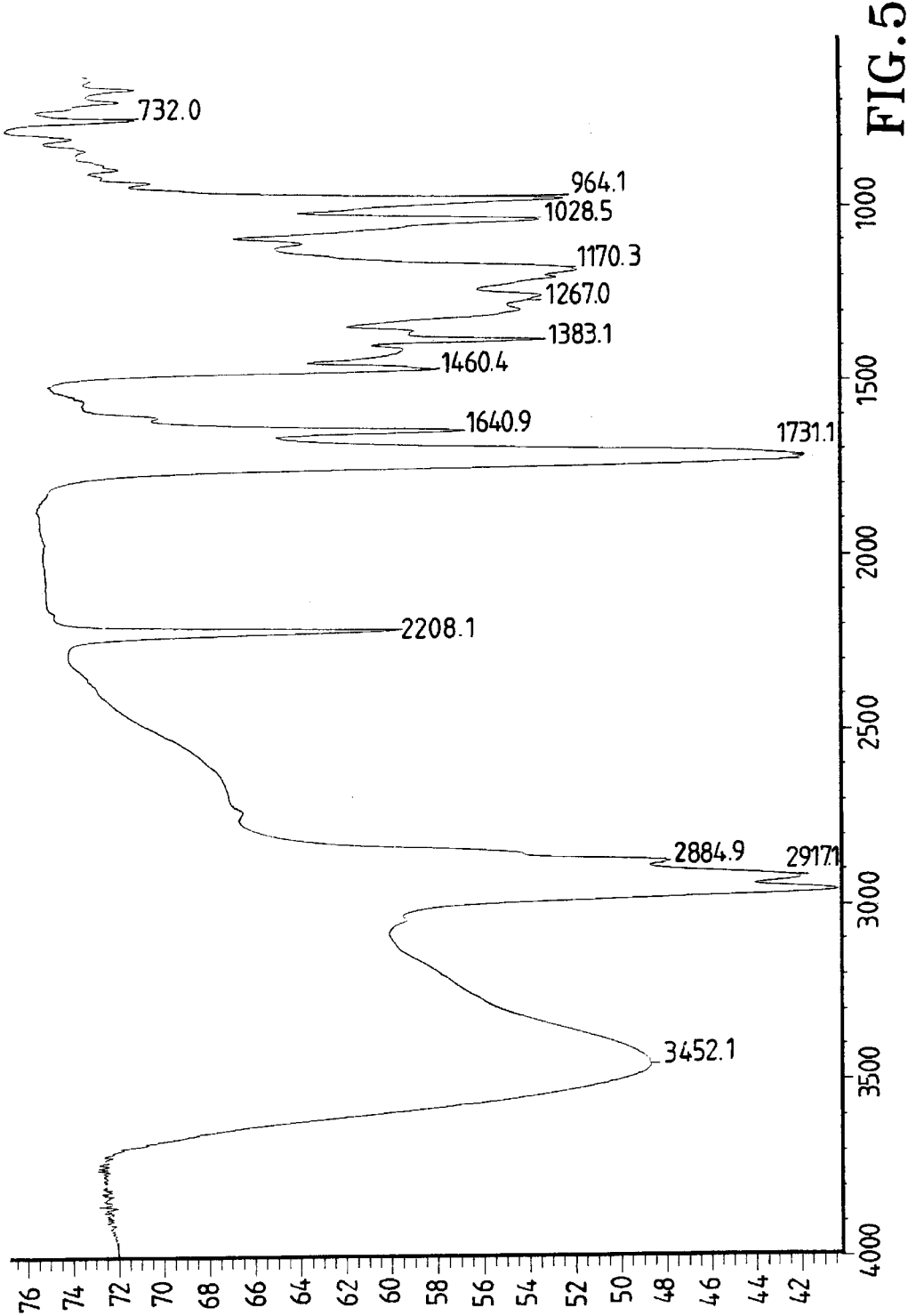
FIG. 5 is the infrared (IR) spectrum of isolated borrelidin.

The resultant product has the $H^1$-NMR and IR spectra as shown in FIGS. 4 and 5, respectively; m.p.: 78° C.; Rf: 0.58 (methanol:$CHCl_3$=1:9; silica); MS: 489 ($M^+FAB$).

EXAMPLE 10

Antifungal Activity of Isolated Borrelidin

Procedures:
1. The antifungal activity of the isolated borrelidin was tested against *P. aphanidermatum, P. splendens, P. sylvaticum, P. capsici* and *Phytophthora ultimum* in vitro.
2. The isolated borrelidin was dissolved in methanol. Pasteurized, molten PDA (50 ml) was allowed to cool to 50° C. and mixed with 0.1 ml of borrelidin in methanol. Each fungal strain was tested at a specific concentration (max. 0.2 mg/l), or diluted concentration. A series of five concentrations was used to determine $EC_{50}$ (the concentration at which 50% fungal growth is inhibited).
3. PDA medium (50 ml) was mixed with 0.1 ml of borrelidin in methanol.
4. The pathogenic fungi (2 mm mass) were inoculated. A microtitration plate added with methanol was used as control. The inhibition (%) was calculated when the control was fully covered with fungal mass, and $EC_{50}$ was determined.

Results:

TABLE 14

| Fungi | Growth Inhibition (%) | | | |
|---|---|---|---|---|
| | 0.2 mg/l | 0.05 mg/l | 0.025 mg/l | $EC_{50}$ (mg/l) |
| *P. aphanidermatum* | 99 | 45 | 14 | 0.06 |
| *P. splendens* | 99 | 70 | 36 | 0.03 |
| *P. sylvaticum* | 100 | 99 | 80 | 0.01 |
| *P. capsici* | 92 | 70 | 41 | 0.027 |
| *P. ultimum* | 83 | 17 | 0 | 0.10 |

What is claimed is:

1. A method for promoting germination of seeds, which comprises applying to the seeds a germination stimulator, which comprises an effective amount of borrelidin together with an agriculturally acceptable carrier, adjuvant or diluent thereof.

* * * * *